(12) United States Patent  (10) Patent No.: US 8,905,957 B1
Kozersky  (45) Date of Patent: Dec. 9, 2014

(54) ADJUSTABLE ORTHOTIC BRACE

(71) Applicant: David J. Kozersky, Columbus, OH (US)

(72) Inventor: David J. Kozersky, Columbus, OH (US)

(*) Notice: Subject to any disclaimer, the term of this patent is extended or adjusted under 35 U.S.C. 154(b) by 0 days.

(21) Appl. No.: 13/660,664

(22) Filed: Oct. 25, 2012

Related U.S. Application Data

(63) Continuation of application No. 12/229,936, filed on Aug. 28, 2008, now abandoned.

(51) Int. Cl.
*A61F 5/00* (2006.01)

(52) U.S. Cl.
USPC .............................................. 602/19; 602/13

(58) Field of Classification Search
USPC ........... 602/13, 19, 36; 128/DIG. 20; 606/237
See application file for complete search history.

(56) References Cited

U.S. PATENT DOCUMENTS

| | | | |
|---|---|---|---|
| 2,100,964 A | 11/1937 | Kendrick | |
| 3,926,183 A | 12/1975 | Sprio | |
| 3,927,665 A | 12/1975 | Wax | |
| 4,175,553 A | 11/1979 | Rosenberg | |
| 4,202,327 A | 5/1980 | Glancy | |
| 4,459,979 A | 7/1984 | Lewis, Jr. | |
| 4,475,543 A | 10/1984 | Brooks et al. | |
| 4,508,110 A | 4/1985 | Modglin | |
| 4,559,933 A | 12/1985 | Batard et al. | |
| 4,622,957 A * | 11/1986 | Curlee | 602/13 |
| 5,074,288 A | 12/1991 | Miller | |
| 5,188,585 A | 2/1993 | Peters | |
| 5,362,304 A | 11/1994 | Varn | |
| 5,967,998 A | 10/1999 | Modglin | |
| 6,478,759 B1 | 11/2002 | Modglin et al. | |
| 6,964,644 B1 * | 11/2005 | Garth | 602/19 |
| 7,048,707 B2 * | 5/2006 | Schwenn et al. | 602/26 |

* cited by examiner

*Primary Examiner* — Patricia Bianco
*Assistant Examiner* — Keri J Nelson
(74) *Attorney, Agent, or Firm* — Roger A. Gilcrest

(57) ABSTRACT

The present invention includes an orthotic brace which offers advantages in being able to be adjusted to fit the small of the back of a specific wearer, and may attain an infinite number of positions within its range of motion, while providing effective reinforced lumbar support.

11 Claims, 5 Drawing Sheets

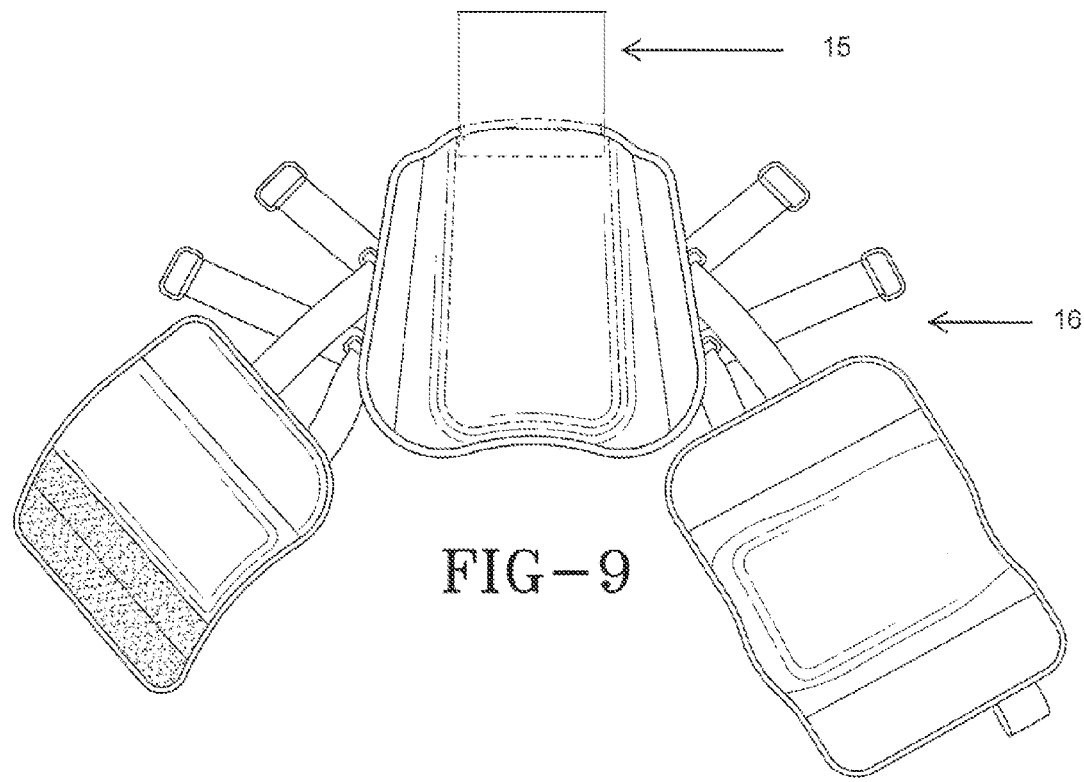
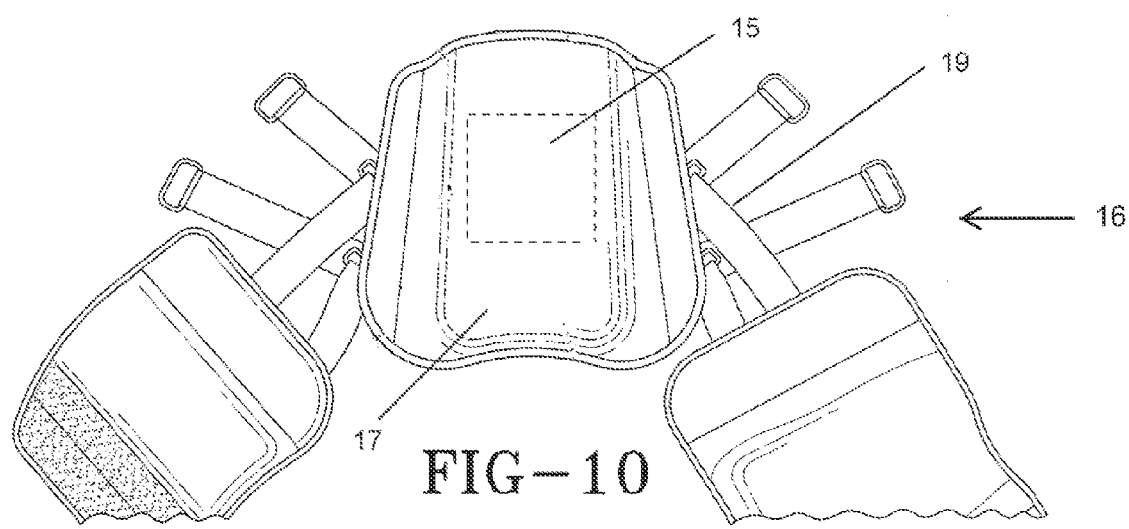

ADJUSTABLE ORTHOTIC BRACE

RELATED APPLICATION DATA

This application is a continuation of U.S. application Ser. No. 12/229,936, filed Aug. 28, 2008, which is incorporated herein in its entirety by reference.

TECHNICAL FIELD FOR THE INVENTION

The present invention relates to an adjustable orthotic brace and especially to a flexible orthopedic brace providing for convenient adjustment to fit a wearer by adjustment to multiple configurations.

BACKGROUND OF THE INVENTION

Several prior art orthotic braces feature front and rear panels to provide lumbar support to the patient.

For instance, in U.S. Pat. Nos. 6,478,759 and 5,967,998, hereby incorporated herein by reference, a single front support panel is attached to one or more rear panels to provide lumbar support to the patient upon closure. Devices of this type provide better support in comparison to belt-type devices. These devices may feature a reinforcement insert, typically of relatively rigid plastic, inserted into a soft material rear portion which in turn is connected to a front portion by straps. Other braces of the prior art include those described in U.S. Pat. No. 4,202,327 having a number of straps for connecting right and left sections with the straps secured to the jacket with hook-and-loop strips. U.S. Pat. No. 4,508,110 describes a jacket-type orthoses that limits motion in the thoracic or lumbo-sacral areas and uses a rigid orthoses design that may be adjusted by a patient pulling on a plurality of laces, each attached to a short strap having hook-and-loop material thereon which is used to attach the straps to predetermined positions on the rigid brace members. Other prior art U.S. patents for orthoses include U.S. Pat. No. 4,475,543, for a lumbo-sacral brace using an elastic belt fastened with a pouch in combination with a semi-wrap-around polyurethane foam splint cured in place in the pouch; U.S. Pat. No. 2,100,964, describing a surgical belt is illustrated in which a plurality of laces are interconnected to a single strap on either side thereof; and U.S. Pat. No. 3,926,183, disclosing a dorsal lumbo sacral support combines elastic and non-elastic straps in a support device for a person's back, thoracic or pelvic areas.

U.S. Pat. No. 3,927,665 relates to a lumbo-sacral support having an elastic body encircling band and inelastic tensioning system, while U.S. Pat. No. 5,074,288 illustrates a soft body brace attached to a patient with a plurality of straps to provide a back support system with interchangeable and positionally adjustable orthotic support.

U.S. Pat. No. 4,175,553 is also a lumbo-sacral orthosis orthopedic support for encircling the torso and has a plurality of straps, and U.S. Pat. No. 4,459,979 is an orthopedic appliance made of resilient material conforming to the lower back of a person and uses a plurality of adjustable straps. U.S. Pat. No. 5,362,304 discloses a thoracic lumbar sacral orthosis device formed as a jacket and has support plates which can attach thereto, and U.S. Pat. No. 5,188,585 concerns a lumbo-sacral orthopedic support which encircles the torso of a patient and has adjustable strap portions. U.S. Pat. No. 4,559,933 describes an orthopedic lumbo-sacral corset using semi-rigid elements and inflatable pads.

The foregoing patents are hereby incorporated herein by reference.

One of the problems with these types of braces is that the reinforcement inserts placed in the rear panel portion of an orthotic brace typically are relatively stiff and cannot be formed to fit the small of the back of a particular patient. The patient must use an array of straps on at least one side of the brace to tilt the rear panel containing the reinforcement insert.

While more malleable materials might be used to conform to the shape of a particular patient's back, these softer materials alone typically are incapable of transmitting enough static force to provide lumbar support to the patient.

Accordingly, in light of the aforementioned shortcomings of currently available orthotic braces, there is a need for a flexible lumbar orthosis which can be adjusted on the patient so as to conform to the back of a patient to provide a more customized fit, without sacrificing lumbar support rigidity, and while easily adjusted without having to adjust the brace by rearranging the straps or other portion of the brace.

SUMMARY OF THE INVENTION

The present invention includes an orthotic brace which offers advantages in being able to be adjusted to fit the small of the back of a specific wearer, and may attain an infinite number of positions within its range of motion, while providing effective reinforced lumbar support.

The present invention includes a flexible lumbo-sacral orthopedic (LSO) brace which fits closely to the patient's torso while being easily attached and tightened in a wide variety of positions for a wide variety of body shapes and provides for optional side splints and lightweight splints removably attachable thereto. The present invention may also be embodied as a thoraco-lumbo-sacral orthopedic (TSLO) brace which typically has a longer rear portion and includes shoulder straps (not shown) which variation is known in the art. Accordingly, as used herein, the term "lumbo-sacral orthopedic brace" shall be understood as including both LSO and TSLO variations. The present invention may be incorporated into any lumbar brace or support device.

The present invention in general terms comprises a lumbar-sacral orthosis comprising in combination, (a) a frontal portion; (b) a lumbar reinforcement portion, the lumbar reinforcement portion having an adjustable portion comprising (1) a relatively rigid outer base portion, (2) a relatively flexible inner portion, the inner portion moveably fixed to the outer base portion so as to be able to be bowed away from the outer base portion, and (3) an inflatable air bladder positioned between the inner portion and the outer base portion, and having an air conduit adapted to reversibly inflate and deflate the air bladder; and (c) at least one strap adapted to connect the frontal portion to the lumbar portion.

The secured position of the outer base portion to the relatively flexible inner portion may be accomplished through any mechanical arrangement that secures the relative position of these two portions while allowing the relatively flexible inner portion to flex with respect to the relatively stiffer outer base portion. This may be done by any mechanical arrangement consistent with the function as described.

The outer and inner portions should be of dimensions, materials and thickness that the inner portion flexes while the outer portion remains substantially unflexed, so that the extension of the inner portion is directional toward the patient's body.

In one variation, the relatively flexible inner portion comprises two or more guide slots disposed on opposing ends thereof, and wherein the inner portion is moveably fixed to the outer base portion by respective guide members extending from the outer base portion through the guide slots.

In another variation, the outer base portion comprises two opposing edges, a portion of each having slot-like structure adapted to slidingly engage the relatively flexible inner portion, and the relatively flexible inner portion slidingly engaged within the structure on the two opposing edges, while allowing the relatively flexible inner portion to flex and move as described.

It is preferred that the lumbo-sacral orthopedic brace additionally comprise at least one strap extending from the frontal portion to the lumbar portion.

Typically and preferably, the lumbar portion will be provided with a pocket and the lumbar reinforcement portion is placed into the pocket, preferably in a removable fashion.

It is also preferred that the brace additionally comprise a hand pump bulb connected to the air conduit.

The outer base portion may be made of any dimensionally stable material, typically rigid enough to provide reinforcement to the lumbar portion of the brace, such as in reinforcement inserts known and used in the art, such as through use of a polymeric material.

Likewise, the relatively flexible inner portion typically will be made of a relatively flexible polymeric material.

In a preferred embodiment, and as a non-limiting example, the outer base portion may be made of any dimensionally stable material such as ABS plastic of at least one-eighth inch, while the relatively flexible inner portion typically will be made of a low density polyethylene of a thickness of about one sixteenth inch. This may vary slightly with the overall size, shape and surface area of the outer base portion and the relatively flexible inner portion, so long as the relatively flexible inner portion flexes with respect to the outer portion.

BRIEF DESCRIPTION OF THE DRAWINGS

FIG. 9 represents a lumbar reinforcement portion and a lumbal-sacral orthosis having a pocket into which a lumbar reinforcement portion may be inserted, in accordance with one embodiment of the present invention.

FIG. 10 represents a lumbal-sacral orthosis having a lumbar reinforcement portion, in accordance with one embodiment of the present invention.

DETAILED DESCRIPTION OF THE PREFERRED EMBODIMENTS

In accordance with the foregoing summary of the invention, the following presents the preferred embodiments of the present invention, which are considered to be the best mode thereof.

Figure 1:
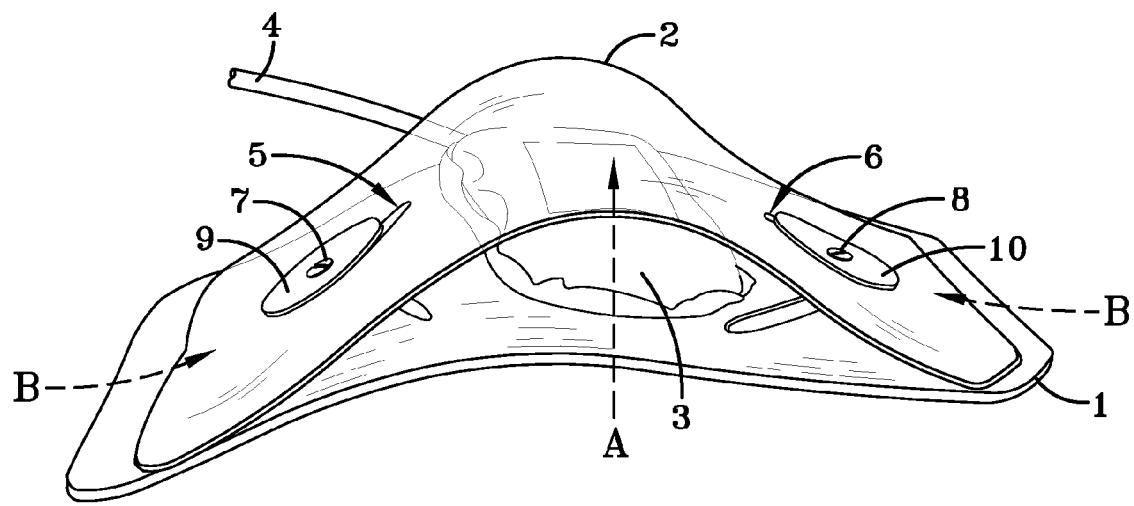
FIG. 1 is an elevation view of a lumbar reinforcement portion in accordance with one embodiment of the present invention, showing the lumbar reinforcement portion in an open, extended configuration.

FIG. 1 is an elevation view of a lumbar reinforcement portion in accordance with one embodiment of the present invention, showing the lumbar reinforcement portion in an open, extended configuration. FIG. 1 shows base outer base portion 1 and relatively flexible inner portion 2, the inner portion moveably fixed to the outer base portion 1 so as to be able to be bowed away from the outer base portion as shown in this view. FIG. 1 also shows inflatable air bladder 3 positioned between the inner portion 2 and the outer base portion 1, and having an air conduit 4 adapted to reverseably inflate and deflate the air bladder 3.

FIG. 1 also shows slots 5 and 6 through which pass bolts or screws 7 and 8 respectively with corresponding plastic washers 9 and 10, to slidingly hold the outer base portion 1 and relatively flexible inner portion 2 in position.

As bladder 3 inflates to expand along direction line A, the relatively flexible inner portion 2 bows so as to be drawn along direction line B.

Figure 2:
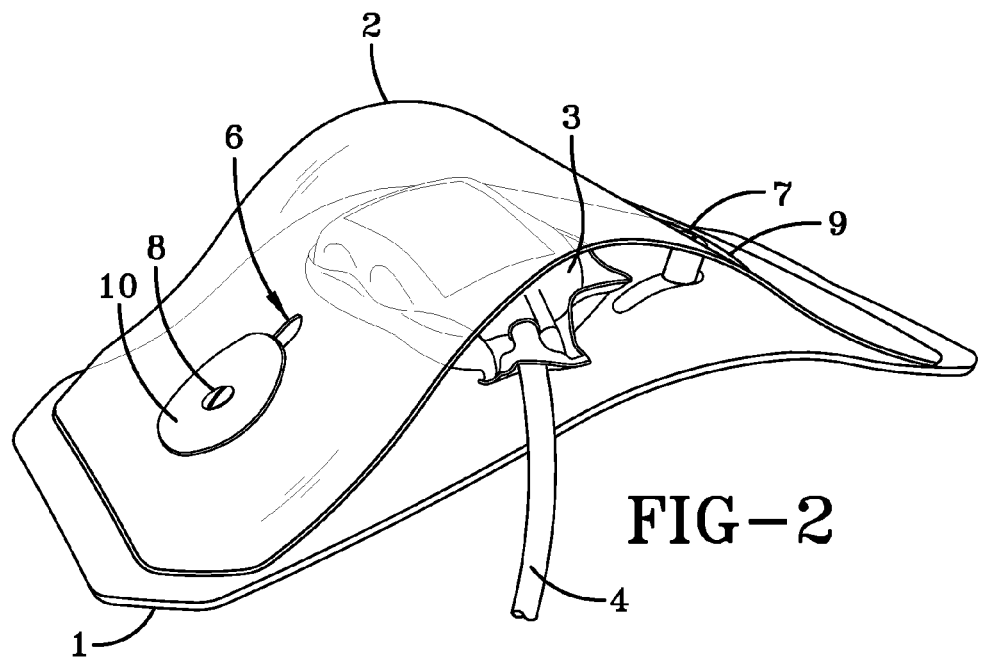
FIG. 2 is an elevation view of the opposite side of a lumbar reinforcement portion shown in FIG. 1, in accordance with one embodiment of the present invention, again showing the lumbar reinforcement portion in an open, extended configuration.

FIG. 2 is an elevation view of the opposite side of a lumbar reinforcement portion shown in FIG. 1, in accordance with one embodiment of the present invention, again showing the lumbar reinforcement portion in an open, extended configuration with the same reference numerals used to indicate the parts thereof.

Figure 3:
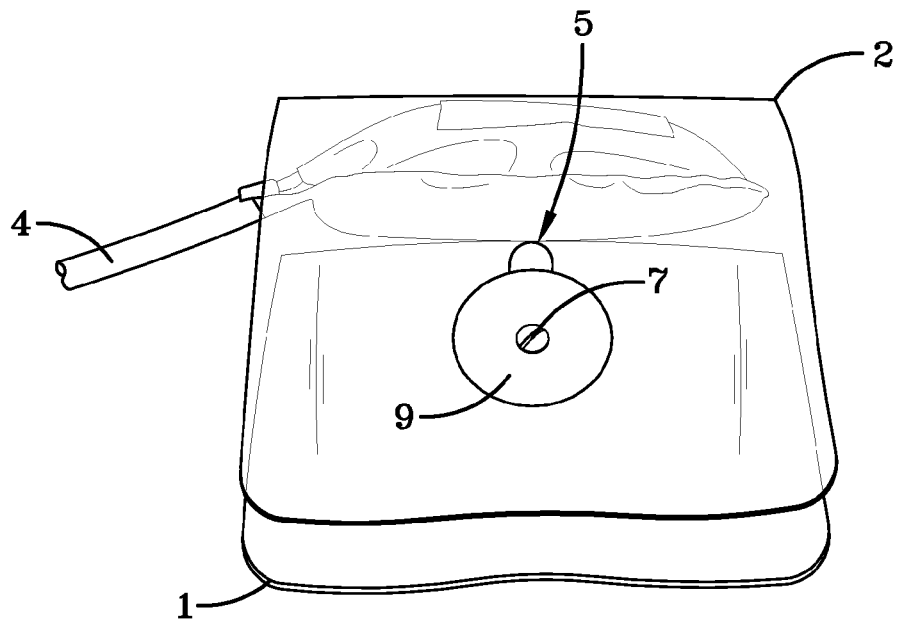
FIG. 3 is a front perspective view of a lumbar reinforcement portion in accordance with one embodiment of the present invention, showing the lumbar reinforcement portion in an open, extended configuration.

FIG. 3 is a front perspective view of a lumbar reinforcement portion in accordance with one embodiment of the present invention, showing the lumbar reinforcement portion in an open, extended configuration, with the same reference numerals used to indicate the parts thereof.

Figure 4:
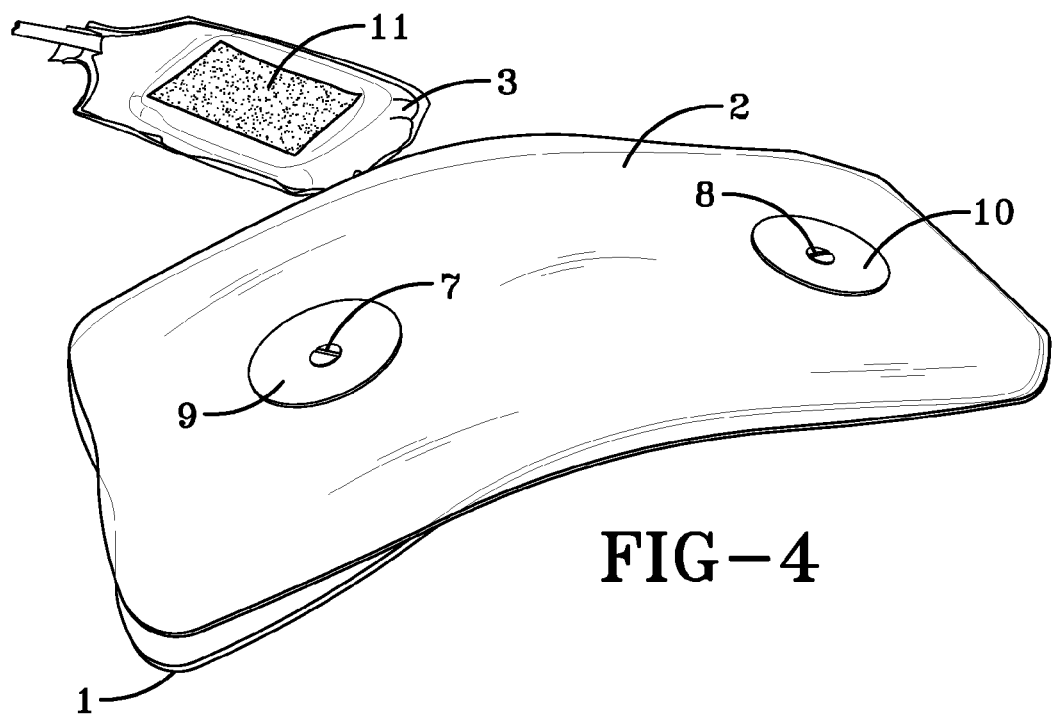
FIG. 4 is a side perspective view of a lumbar reinforcement portion in accordance with one embodiment of the present invention, showing the lumbar reinforcement portion in a closed configuration with the air bladder removed.

FIG. 4 is a side perspective view of a lumbar reinforcement portion in accordance with one embodiment of the present invention, showing the lumbar reinforcement portion in a closed configuration with the air bladder removed, with the same reference numerals used to indicate the parts thereof. If desired, the bladder 3 may be provided with a hook and loop pad 11 to hold it in place between the outer base portion 1 and the relatively flexible inner portion 2, such as by providing a corresponding hook and loop pad (not seen in the Figure) on the base portion 1, to allow the bladder 3 to be inflated while the relatively flexible inner portion 2 may move freely with respect to the bladder 3.

Figure 5:
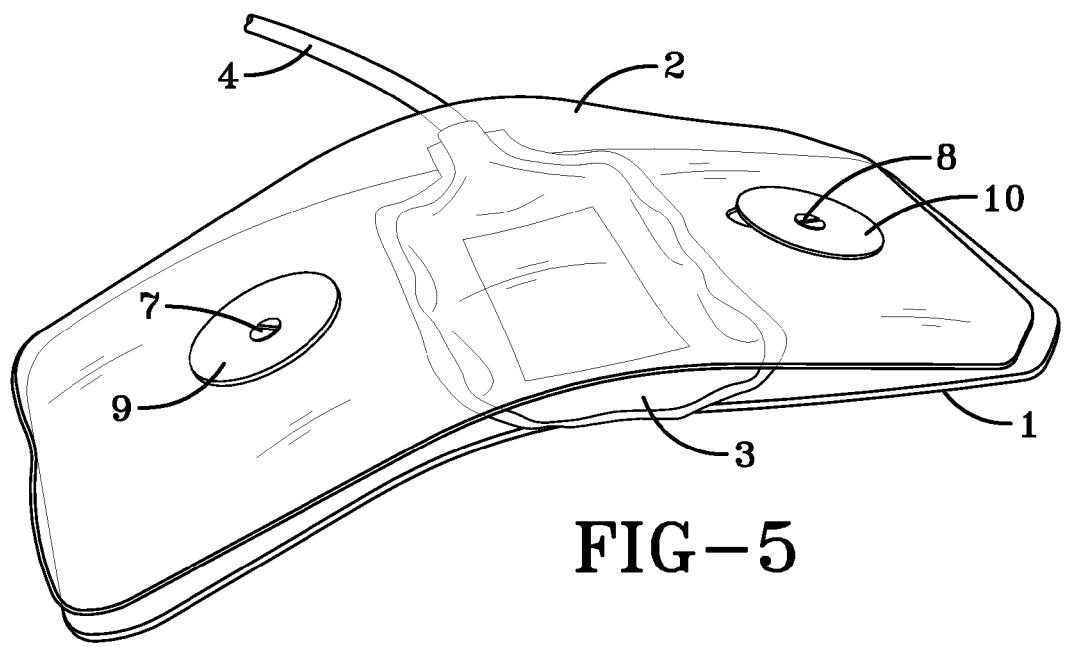
FIG. 5 is a side perspective view of a lumbar reinforcement portion in accordance with one embodiment of the present invention, showing the lumbar reinforcement portion in a closed configuration with the air bladder inserted.

FIG. 5 is a side perspective view of a lumbar reinforcement portion in accordance with one embodiment of the present invention, showing the lumbar reinforcement portion in a closed configuration with the air bladder inserted, with the same reference numerals used to indicate the parts thereof.

Figure 6:
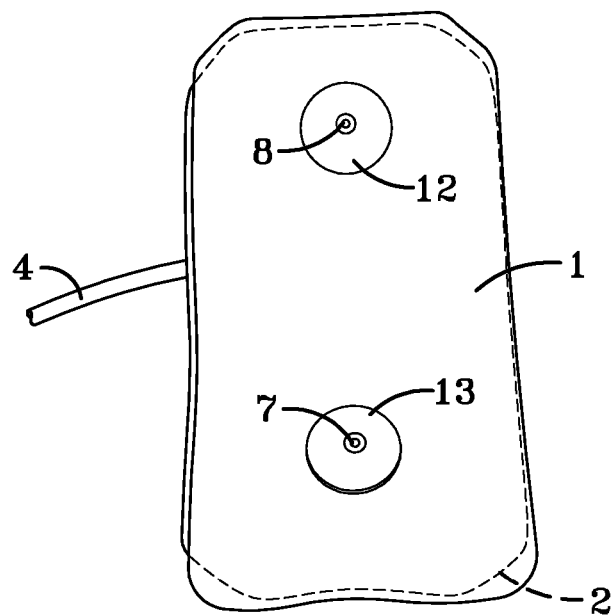
FIG. 6 is a bottom plan view of a lumbar reinforcement portion in accordance with one embodiment of the present invention, showing the lumbar reinforcement portion in a closed configuration with the air bladder inserted.

FIG. 6 is a bottom plan view of a lumbar reinforcement portion in accordance with one embodiment of the present invention, showing the lumbar reinforcement portion in a closed configuration with the air bladder inserted, and with the same reference numerals used to indicate the parts thereof. This view also shows additional plastic washers 12 and 13 that may be used to secure bolts 7 and 8 to the outer base portion 1.

Figure 7:
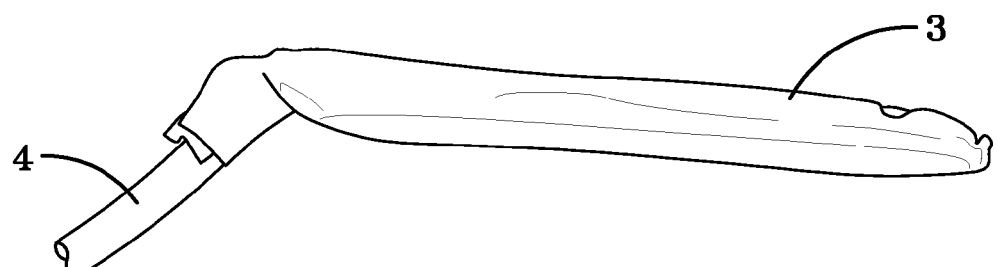
FIG. 7 is a side perspective view of an air bladder used in conjunction with a lumbar reinforcement portion in accordance with one embodiment of the present invention, showing the air bladder deflated.

FIG. 7 is a side perspective view of an air bladder 3, as used in conjunction with a lumbar reinforcement portion in accordance with one embodiment of the present invention, showing the air bladder deflated.

Figure 8:
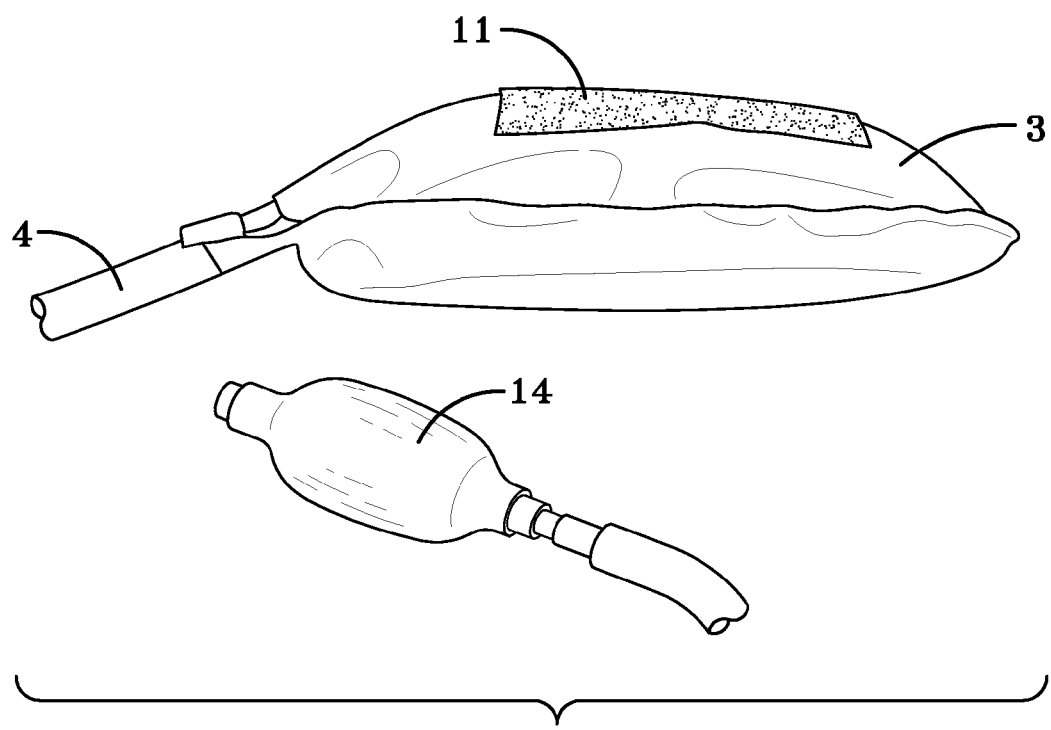
FIG. 8 is a side perspective view of an air bladder and hand pump used in conjunction with a lumbar reinforcement portion in accordance with one embodiment of the present invention, showing the air bladder inflated.

FIG. 8 is a side perspective view of an air bladder 3 with hook and loop fastener 11 and hand pump bulb 14 that may be used in conjunction with a lumbar reinforcement portion in accordance with one embodiment of the present invention, showing the air bladder inflated. The conduit 4 typically is long enough to reach around the torso of the wearer to provide a convenient pumping of the bladder 3 while the brace is being worn. The hand pump bulb 14 may be removable with a valve at the end of the conduit, so that the hand pump bulb 14 may be removed from the brace after adjustment.

FIG. 9 is a representative view of a lumbar reinforcement portion 15 and a lumbal-sacral orthosis 16 having a pocket 17 into which a lumbar reinforcement portion may be inserted in accordance with one embodiment of the present invention. FIG. 9 further shows lumbal-sacral orthosis 16 having a frontal portion 18, strap 19, and a pocket 17 adapted to receive lumbar reinforcement portion 15.

FIG. 10 is representative view of a lumbal-sacral orthosis having a lumbar reinforcement portion in accordance with one embodiment of the present invention. FIG. 10 shows lumbal-sacral orthosis 16 having a lumbar reinforcement portion 15 inserted into pocket 17 of lumbal-sacral orthosis 16. FIG. 10 further shows a lumbal-sacral orthosis having frontal portion 18 and strap 19.

The relatively rigid base portion may be made of a rigid plastic such as ABS plastic, typically of a thickness greater than ⅛ inch.

The relatively flexible inner portion is typically made of a plastic more flexible than the relatively rigid base portion, such as LDPE and is preferably of a thickness less than or equal to that of the relatively rigid base portion, typically about 1/16 inch.

Some of the advantages of the present invention are that the brace provides several of the advantages of prior art braces, while also offering infinite customized adjustment of the brace within a range of movement of the device as provided by the dimensions of the outer base portion 1 and the relatively flexible inner portion 2. The lumbar reinforcement of the present invention has the ability to provide lumbar support that is adjustable in terms of snugness and the degree of support to the lumbar portion of an orthotic brace.

While the invention may be rendered in embodiments in many different forms, there have been shown in the drawings and described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

What is claimed is:

1. A lumbar-sacral orthosis comprising in combination,
    (a) a frontal portion;
    (b) a lumbar reinforcement portion, said lumbar reinforcement portion having an adjustable portion comprising
        (1) a relatively rigid outer base portion,
        (2) a relatively flexible inner portion having two end portions, said inner portion comprises two guide slots disposed on said two end portions, wherein said two end portions are moveably and slidingly fixed to said outer base portion by respective guide members extending from said outer base portion through said guide slots, and wherein said inner portion is configured to bow away from said outer base portion when said guide members slide within said guide slots, and
        (3) an inflatable air bladder positioned between said inner portion and said outer base portion, and having an air conduit adapted to reversibly inflate and deflate said air bladder; and
    (c) at least one strap adapted to connect said frontal portion to said lumbar reinforcement portion.

2. A lumbar-sacral orthosis according to claim 1 additionally comprising a lumbar portion having a pocket and wherein said lumbar reinforcement portion is placed into said pocket.

3. A lumbar-sacral orthosis in accordance with claim 1 additionally comprising a hand pump bulb connected to said air conduit.

4. A lumbar-sacral orthosis in accordance with claim 1 wherein said outer base portion comprises a polymer material.

5. A lumbar-sacral orthosis in accordance with claim 1 wherein said inner portion comprises a polymer material.

6. A lumbar-sacral orthosis according to claim 1 wherein said outer base portion comprises two opposing outer base edges adapted to slidingly engage said two end portions.

7. A lumbar-sacral orthosis according to claim 6 wherein said inner portion comprises two opposing inner portion edges that are configured to move with respect to said two opposing outer base edges.

8. A lumbar reinforcement device for an orthopedic brace, comprising:
    an outer base portion;
    a flexible inner portion having a first end portion and a second end portion;
    an inflatable bladder disposed between said outer base portion and said inner portion, wherein said bladder is configured to inflate to permit said inner portion to bow away from said outer base portion; and
    at least one guide member that attaches said outer base portion to said inner portion, wherein one of said outer base portion and said inner portion comprises at least one guide slot configured to receive said at least one guide member to permit said at least one guide member to move along said at least one guide slot such that said at least one guide member is coupled to, and configured to slide relative to, one of said outer base portion and said inner portion;
    wherein said inner portion is configured to bow away from said outer base portion when said at least one guide member slides within said at least one guide slot.

9. The lumbar reinforcement device of claim 8, further comprising an air conduit adapted to reversibly inflate and deflate said bladder.

10. The lumbar reinforcement device of claim 8, wherein said at least one guide member is coupled to, and configured to slide relative to, each of said outer base portion and said inner portion.

11. The lumbar reinforcement device of claim 10, wherein each of said outer base portion and said inner portion comprise at least one guide slot configured to receive said at least one guide member to permit said at least one guide member to move along said at least one guide slot.

\* \* \* \* \*